US012667394B2

(12) United States Patent
Biedermann et al.

(10) Patent No.: US 12,667,394 B2
(45) Date of Patent: Jun. 30, 2026

(54) INSTRUMENT FOR USE IN SURGERY

(71) Applicant: BIEDERMANN TECHNOLOGIES GMBH & CO. KG, Donaueschingen (DE)

(72) Inventors: Timo Biedermann, Trossingen (DE); Markku Biedermann, Key Biscayne, FL (US); Achim Schünemann, Villingen-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 70 days.

(21) Appl. No.: 18/664,782

(22) Filed: May 15, 2024

(65) Prior Publication Data

US 2024/0366272 A1 Nov. 7, 2024

Related U.S. Application Data

(63) Continuation of application No. 18/056,637, filed on Nov. 17, 2022, now Pat. No. 12,004,783.

(Continued)

(30) Foreign Application Priority Data

Nov. 18, 2021 (EP) ..................................... 21208986

(51) Int. Cl.
A61B 17/88 (2006.01)
A61B 17/04 (2006.01)
(Continued)

(52) U.S. Cl.
CPC ...... A61B 17/7082 (2013.01); A61B 17/0482 (2013.01); A61B 17/864 (2013.01)

(58) Field of Classification Search
CPC ............ A61B 17/7082; A61B 17/0482; A61B 17/864
(Continued)

(56) References Cited

U.S. PATENT DOCUMENTS 10,105,165 B2 10/2018 Biedermann et al.
10,433,883 B2 10/2019 DiVincenzo et al.
(Continued)

FOREIGN PATENT DOCUMENTS

WO WO 2016/166662 A1 10/2016

OTHER PUBLICATIONS

Extended European Search Report for Application No. 21208986.6, mailed May 25, 2022, 10 pages.

*Primary Examiner* — Eduardo C Robert
*Assistant Examiner* — David C Comstock
(74) *Attorney, Agent, or Firm* — Womble Bond Dickinson (US) LLP

(57) ABSTRACT

An instrument for use in surgery includes a hollow shaft connectable to a drive shaft of a bone anchor insertion device in a rotationally fixed manner, a needle holder configured to hold a needle and movable axially relative to the hollow shaft, an actuator rotatable relative to the hollow shaft, and a transmission member connectable to the needle holder and movable axially relative to the actuator. The transmission member is positionable around at least part of the hollow shaft and includes a first advancement surface engageable with a second advancement surface of the hollow shaft to convert a rotational movement of the actuator into axial movement of the needle holder relative to the hollow shaft for axially advancing and retracting the needle held by the needle holder.

20 Claims, 13 Drawing Sheets

Related U.S. Application Data

(60) Provisional application No. 63/280,765, filed on Nov. 18, 2021.

(51) Int. Cl.
*A61B 17/70* (2006.01)
*A61B 17/86* (2006.01)

(58) Field of Classification Search
USPC .......................... 606/86 A, 279, 99, 102, 104
See application file for complete search history.

(56) References Cited

U.S. PATENT DOCUMENTS

| | | | |
|---|---|---|---|
| 12,004,783 B2 * | 6/2024 | Biedermann ...... | A61B 17/8872 |
| 2006/0248988 A1 | 11/2006 | Bennett | |
| 2009/0228013 A1 | 9/2009 | Bourque et al. | |
| 2012/0004665 A1 | 1/2012 | Defossez et al. | |
| 2012/0253355 A1 | 10/2012 | Murray et al. | |
| 2014/0276892 A1 | 9/2014 | Pakzaban et al. | |
| 2014/0277164 A1 * | 9/2014 | Ramsay ............. | A61B 17/7076 |
| | | | 606/279 |
| 2018/0014862 A1 * | 1/2018 | Raina ................... | A61B 17/708 |
| 2018/0132920 A1 | 5/2018 | Vikinsky et al. | |
| 2018/0368893 A1 | 12/2018 | DiVincenzo et al. | |
| 2019/0125421 A1 | 5/2019 | Smith et al. | |
| 2020/0100824 A1 * | 4/2020 | DiVincenzo ....... | A61B 17/7082 |
| 2020/0281608 A1 | 9/2020 | Sharifi-Mehr et al. | |
| 2020/0390486 A1 | 12/2020 | Rodriguez et al. | |
| 2021/0228245 A1 | 7/2021 | Geist et al. | |
| 2022/0280206 A1 | 9/2022 | Gladieux et al. | |

* cited by examiner

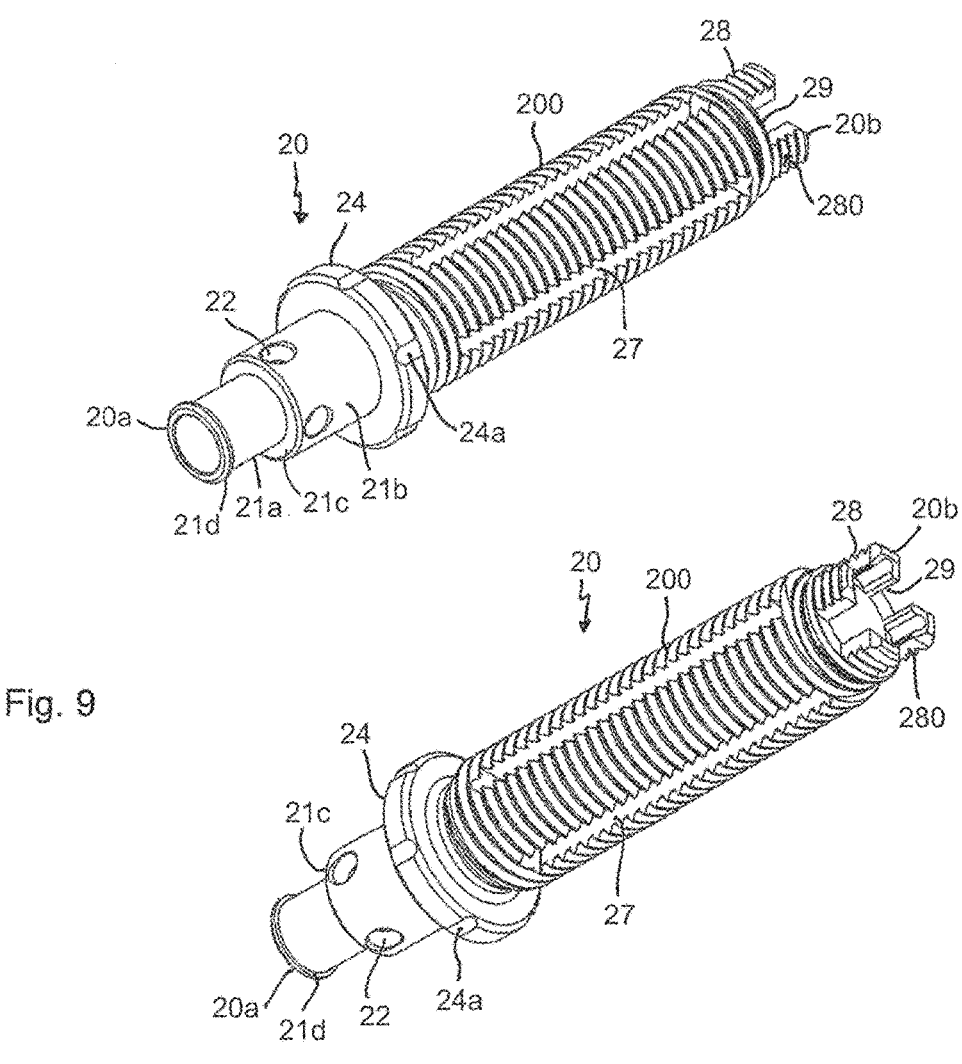
Fig. 9
Fig. 10
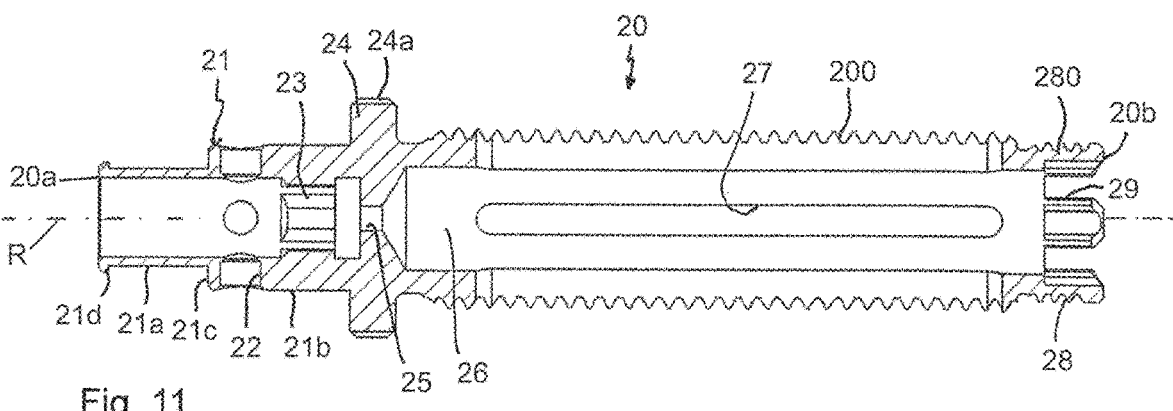
Fig. 11

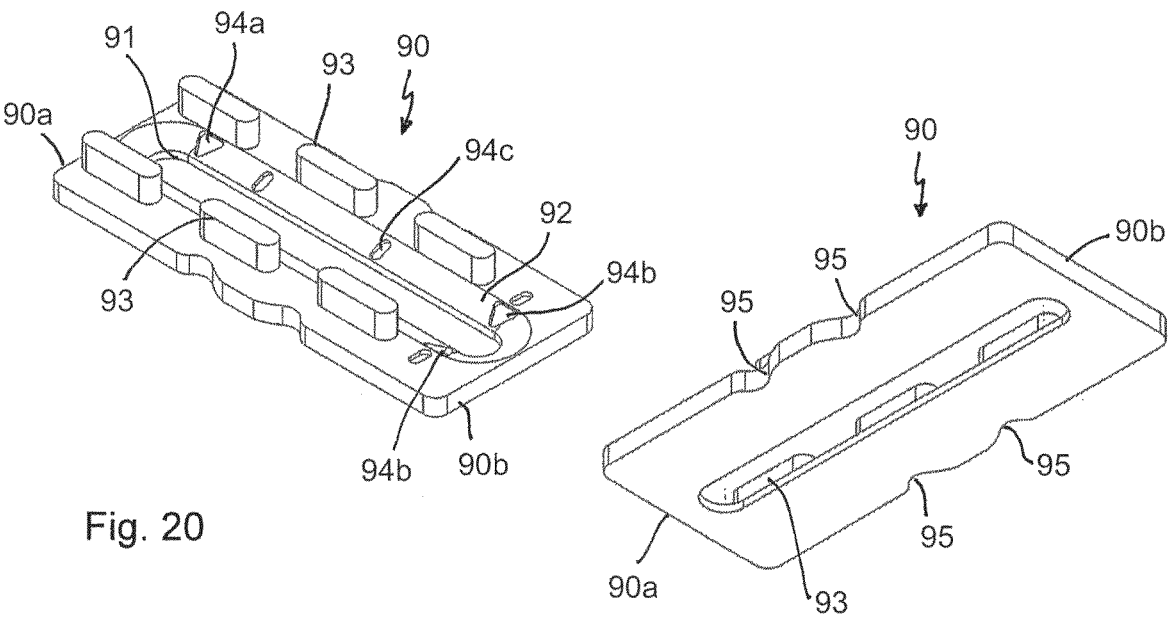
Fig. 20
Fig. 21
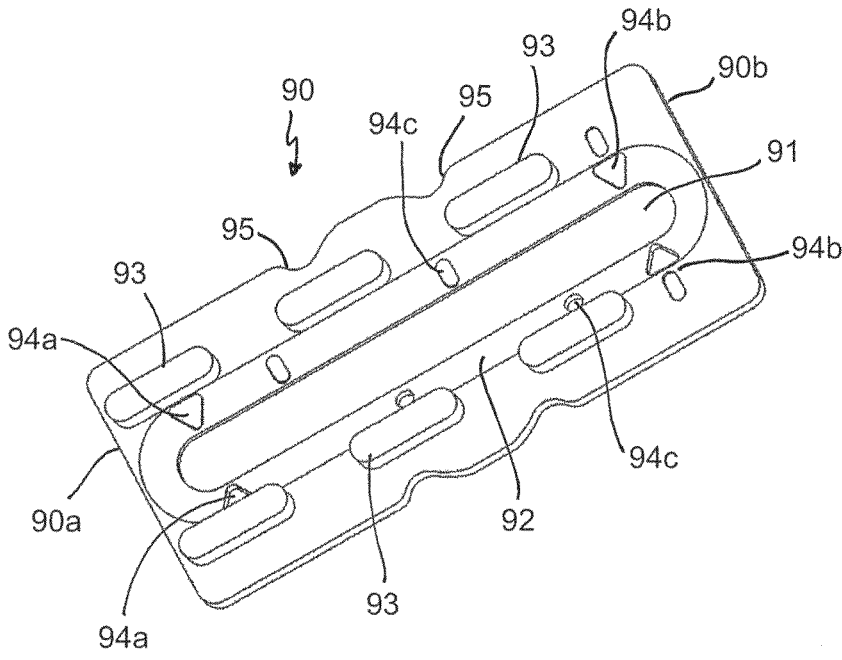
Fig. 22

INSTRUMENT FOR USE IN SURGERY

CROSS-REFERENCE TO RELATED APPLICATION(S)

This application is a continuation of U.S. patent application Ser. No. 18/056,637, filed Nov. 17, 2022, which claims priority to and the benefit of U.S. Provisional Patent Application No. 63/280,765, filed Nov. 18, 2021, the contents of which are hereby incorporated by reference in their entirety, and claims priority from European Patent Application EP 21 208 986.6, filed Nov. 18, 2021, the contents of which are hereby incorporated by reference in their entirety.

BACKGROUND

Field

The application relates to an instrument for use in surgery, in particular, in connection with a bone anchor insertion device. With the instrument, a position of a needle relative to the bone anchor can be adjusted. Further, the invention relates to a surgical instrument including the bone anchor insertion device and the aforementioned instrument. The surgical instrument may in particular be used in musculo-skeletal surgery, and more particularly in spinal surgery.

Description of Related Art

In surgery of the spine, a known technique involves the use of Jamshidi needles for inserting Kirschner wires (K-wires), which may be used for the placement of bone anchors such as pedicle screws. According to the known method, first, a small incision is made in the skin of the patient. After that, a Jamshidi needle including a tiny awl is advanced through the incision to the bone. A bore is prepared by hammering and turning the Jamshidi needle back and forth and then the awl is removed. Subsequently, a K-wire is placed into the hole and the Jamshidi needle is removed. A thread cutter is guided by the K-wire to the hole, and a thread is cut with the thread cutter. After cutting the thread, the thread cutter is screwed back. Finally, a cannulated bone screw is guided by the K-wire to, and screwed into, the threaded hole. As a last step, the K-wire is removed. In total, these steps require the use of several instruments and several instrument passes and may be time consuming, especially in cases where many threaded bores have to be prepared.

A bone anchor insertion device for holding and inserting a bone anchor into the bone, in particular for use with a pedicle screw, is known, for example, from U.S. Pat. No. 10,105,165 B2. The bone anchor insertion device includes a holding member with a seat for holding the head of the bone anchor, the holding member having two arms that are configured to encompass the head of the bone anchor, and a drive shaft for engaging the head of the bone anchor to screw the bone anchor into bone, and a displacement member acting onto the holding member such that the holding member can assume a first configuration in which the head can enter the seat and a second configuration in which the head is held in the seat and the shank of the bone anchor can be screwed into bone.

U.S. Pat. No. 10,433,883 B2 describes surgical instruments for delivering bone anchor assemblies into bone. Use of these assemblies can eliminate one or more of the steps in a conventional bone anchor installation procedure. The surgical instrument includes a handle assembly having an elongate shaft extending distally therefrom. The handle assembly can be configured to axially translate a carrier assembly that secures a stylet extending therethrough. Translation of the stylet can be made relative to a distal end of the elongate shaft.

SUMMARY

It is an object of the invention to provide an improved instrument that allows a number of surgical steps to be reduced and that makes certain surgical steps more efficient.

According to a first aspect of the invention, an instrument for use in surgery, in particular, in connection with a bone anchor insertion device, includes a hollow shaft configured to connect to the drive shaft of a bone anchor insertion device, a needle holder configured to receive a needle and to be translated with respect to the hollow shaft, an actuator rotatable with respect to the hollow shaft, and a transmission member configured to be coupled to the needle holder and to convert a rotational movement of the actuator to a translational movement of the needle holder to advance and retract the needle. The transmission member has a first advancement structure that is configured to engage a second advancement structure provided at the hollow shaft for effecting the translational movement of the needle holder.

The term needle as used herein includes any elongate member that may extend through a cannulated shank of a bone anchor such as, for example, a Jamshidi needle, an awl, a stylet, a needle of a syringe, and others.

With the instrument, the needle can remain at a fixed position during insertion of the shank of the bone anchor in bone. A needle of a fixed length may be used together with bone anchors with different shank lengths. The length of the shank of the bone anchor used with the instrument can be set on a first scale and displayed on the instrument. Moreover, the length of the needle portion that protrudes out of the tip of the shank can be adjusted and displayed on a second scale on the instrument. Hence, an adjustment of the needle position can be carried out easily and safely.

The position of the tip of the needle in the axial direction relative to the tip of the bone anchor can be adjusted in a stepless manner or incrementally. The travel path of the needle may be around 50 mm to 70 mm. Once a position of the needle has been adjusted, this position can be maintained and the shank of the bone anchor can be screwed into the bone. Removal and/or exchange of the needle, if necessary, can be carried out in a simple and time efficient manner. It may also be possible to use the instrument with needles of different type and/or with needles of different length.

The instrument is compact. A cavity formed in the handle portion that drives the drive shaft of the shank inserter is used for housing the needle advancement mechanism and defines a path of translation of the needle holder.

The instrument may be coupled to any bone insertion device, which also may be called a shank inserter, and which includes a drive shaft to engage and rotate a bone anchor with a threaded shank into bone. Such a shank inserter may have a standard coupling at the rear end of the drive shaft, for example, a ¼ inch square connection portion, that can be coupled to the instrument via a standard coupling used for ¼ inch connection portions. Hence, the instrument can form a part of a modular system and can preferably be selectively coupled to different shank inserters. Moreover, the instrument may be used together with an adapter carrying a navigation instrument for computer aided imaging and/or navigation or robotics.

With the instrument according to embodiments of the invention, various techniques for anchoring a bone anchor in bone may be realized. In particular the instrument may be used in minimally invasive surgery (MIS), and preferably using bone anchors with a self-cutting thread.

An embodiment of a method of use includes at least the steps of connecting the instrument to a drive shaft of another instrument for inserting a bone anchor into bone before or after connecting a cannulated bone anchor to the drive shaft, inserting a needle into the instrument and fixing the needle, translating the needle via the actuator such that a tip of the needle extends out of the tip of the bone anchor to a desired distance, inserting the needle into bone, preferably further translating the needle relative to the bone anchor to a desired depth, and inserting the bone anchor along the needle by rotating the handle portion. Afterwards, the needle may be removed from the bone anchor before removing the shank inserter with the instrument, or simultaneously therewith. The method may further include a step of setting the shank length of the bone anchor used on a first scale and adjusting the length of the needle that protrudes out of the bone anchor on a second scale.

BRIEF DESCRIPTION OF THE DRAWINGS

Further features and advantages of the invention will become apparent from the description of embodiments by means of the accompanying drawings. In the drawings:

FIG. 9 shows a perspective view from a front end of a hollow shaft that is part of the instrument of FIGS. 4 to 8.

FIG. 10 shows a perspective view from a rear end of the hollow shaft of FIG. 9.

FIG. 11 shows a cross-sectional view of the hollow shaft of FIGS. 9 and 10, the cross-section taken in a plane including a central longitudinal axis of the hollow shaft.

FIG. 20 shows a perspective view from a top of a shank length and needle position indication device of the instrument of FIGS. 14 to 18.

FIG. 21 shows a perspective view from a bottom of the shank length and needle position indication device of FIG. 20.

FIG. 22 shows another perspective view from the top of the shank length and needle position indication device of FIGS. 20 and 21.

DETAILED DESCRIPTION

Figure 1:
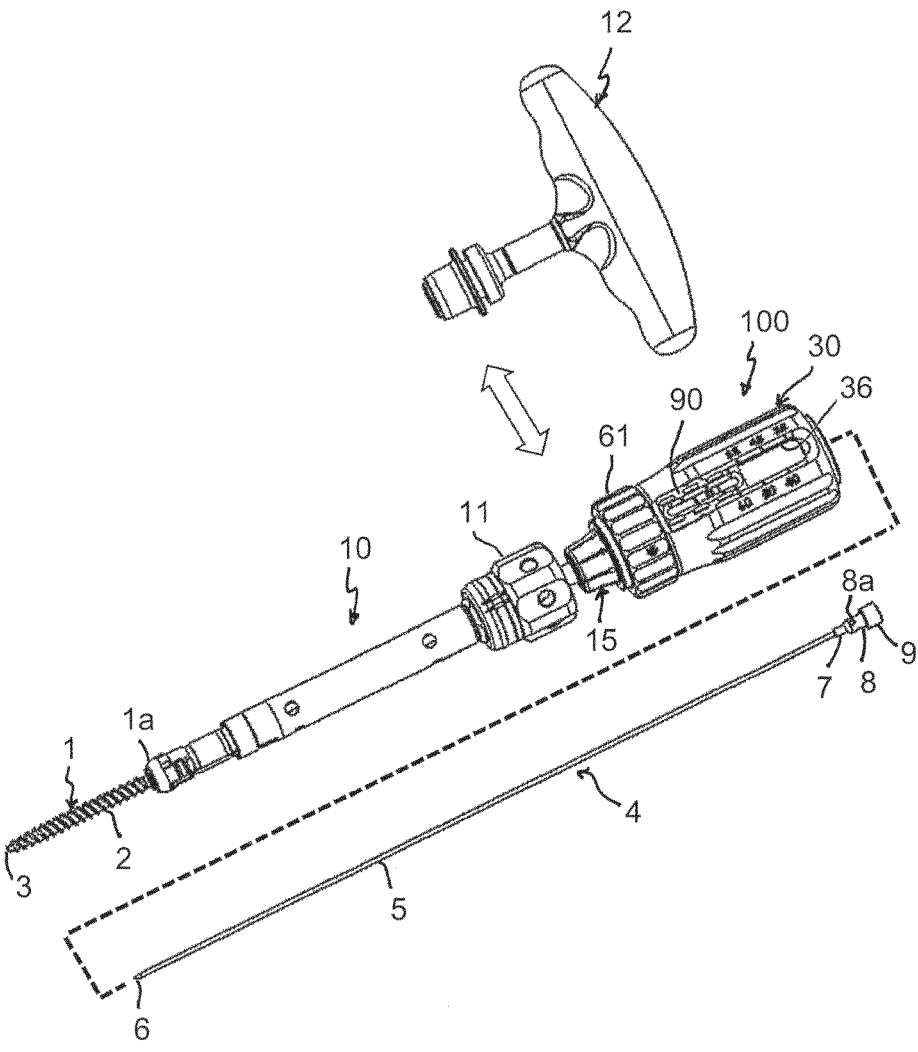
FIG. 1 shows a perspective exploded view of an embodiment of the instrument, a shank inserter, and a bone anchor attached to the shank inserter.
Figures 2, 3:
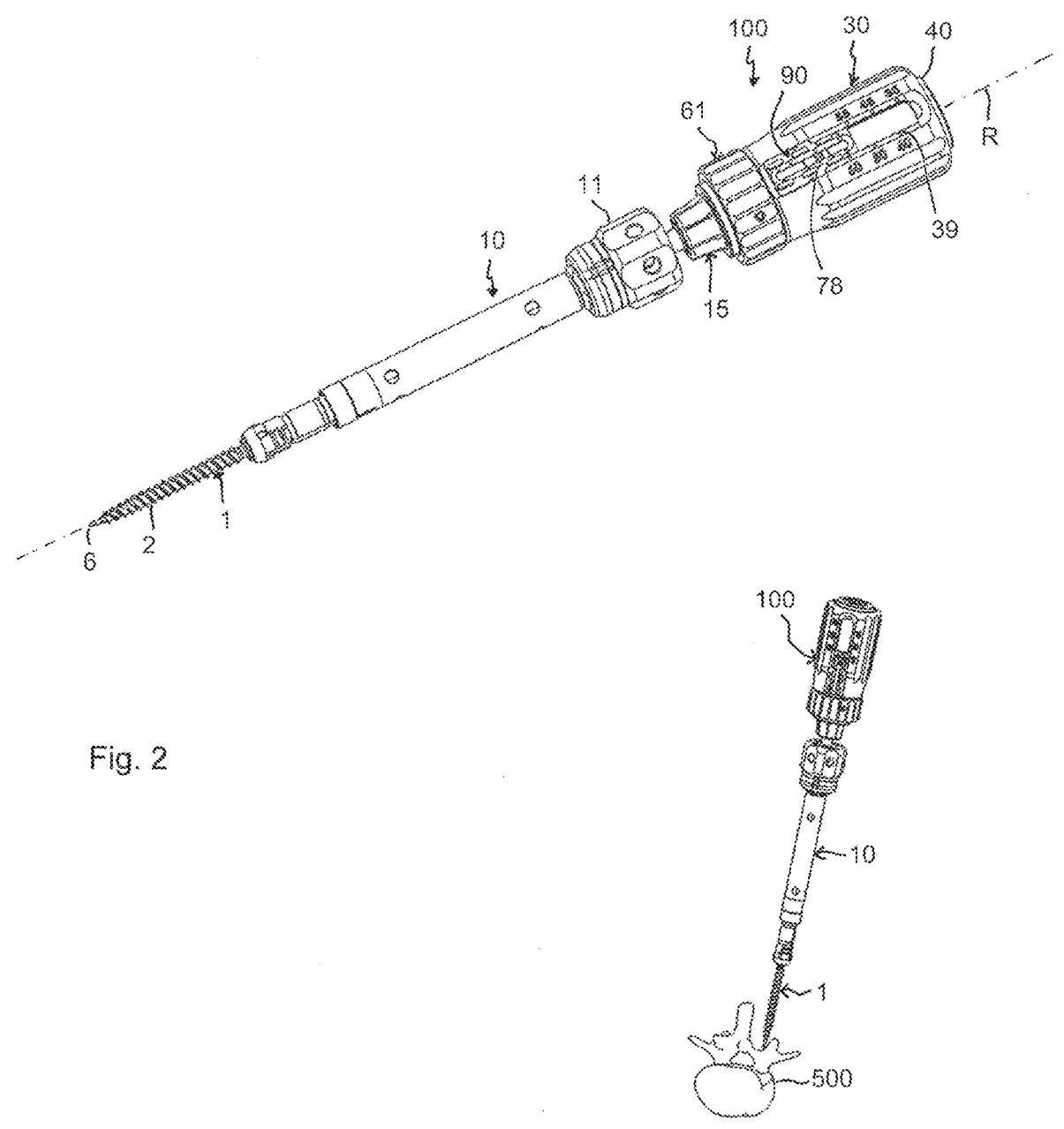
FIG. 2 shows a perspective view of the instrument and the shank inserter of FIG. 1 in an assembled state.
FIG. 3 shows a perspective view of the instrument and the shank inserter of FIGS. 1 and 2 with the bone anchor, prior to insertion of the bone anchor in a vertebra.

Referring to FIGS. 1 to 3, an instrument 100 is configured to be used with a surgical instrument, such as a shank inserter 10, that is adapted to insert a bone anchor 1 into bone. The bone anchor 1 usually has a threaded shank 2 with a tip 3 and may also have a head (not shown) at the end of the shank 2 opposite the tip 3. For example, the bone anchor may be part of a polyaxial bone anchoring device, wherein the head of the bone anchor is held in a receiving part 1a. A needle 4 may be used to place the bone anchor 1 at the desired position on the bone surface and to prepare a tiny hole in the bone that defines the insertion path for the bone anchor 1. For this purpose, the bone anchor 1 may be cannulated so that the needle 4 can extend through the bone anchor 1 from the head to the tip 3. The shank inserter 10 may be any known bone anchor insertion device. Such a shank inserter 10 is configured to engage the bone anchor 1, usually at the head, with a front end of a drive shaft (not shown in detail), so that torque can be transmitted via the drive shaft to the shank 2 to screw the shank 2 into the bone. The drive shaft may have a connection portion, for example, with a polygon outer contour or a square end such as a ¼ inch connection, at its rear end that is shaped and sized to permit quick connection to and release from other instrument parts, such as a T-handle 11 or another type of handle or adapters. A gripping portion 12, such as a thickened portion with axial grooves, may also be provided for the shank inserter 10. To allow the use of the needle 4, the drive shaft is cannulated. This permits the needle 4 to extend completely through the drive shaft and through the bone anchor 1. It shall be noted that the shank inserter may also include only a drive shaft, without other holding or counter holding features that engage the bone anchor.

Figure 4:
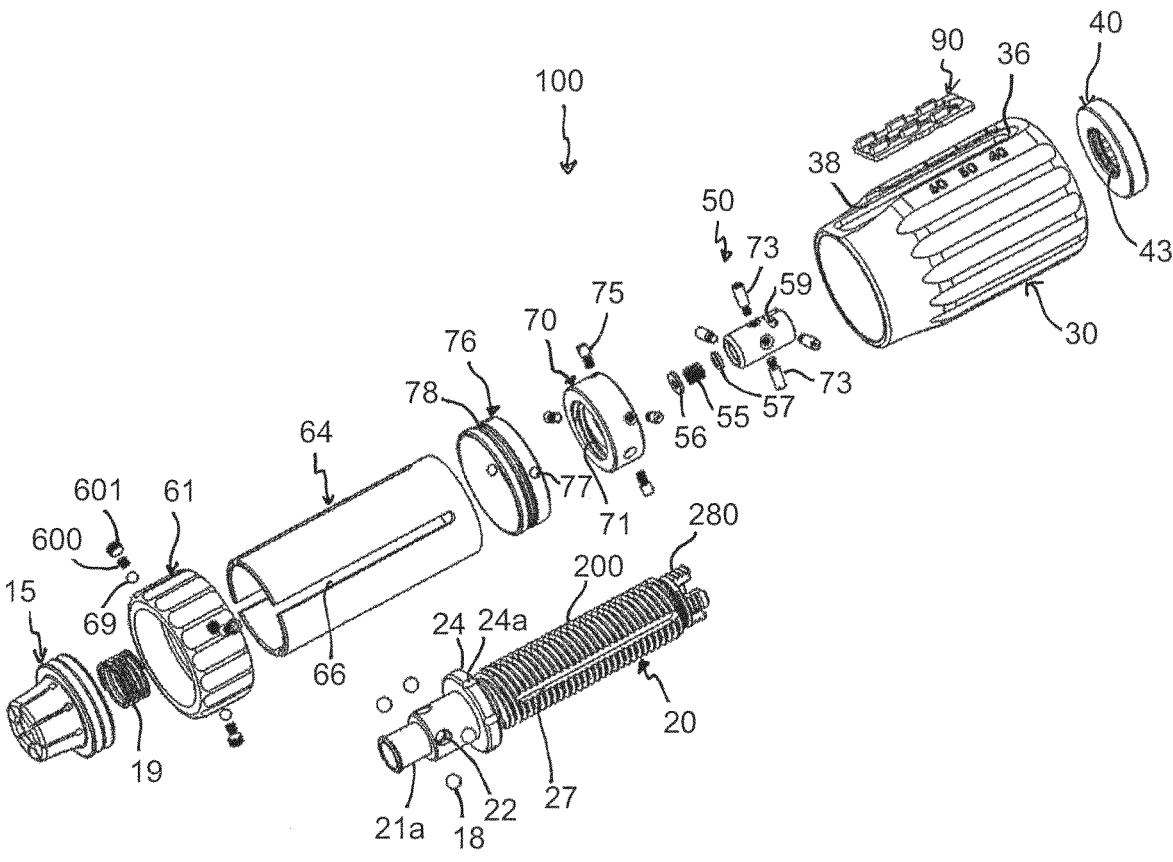
FIG. 4 shows a perspective exploded view of the instrument shown in FIGS. 1 to 3.
Figure 5:
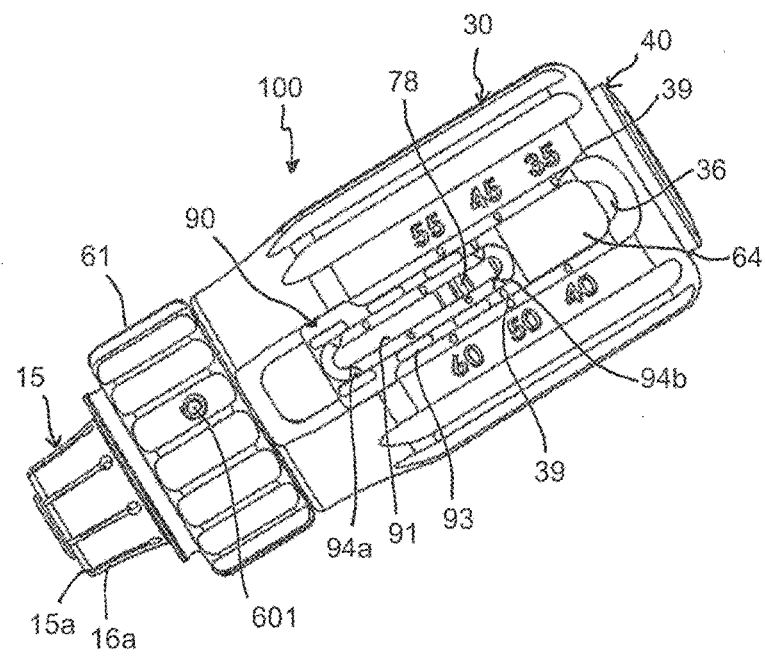
FIG. 5 shows a perspective view of the instrument of FIG. 4 in an assembled state.
Figure 6:
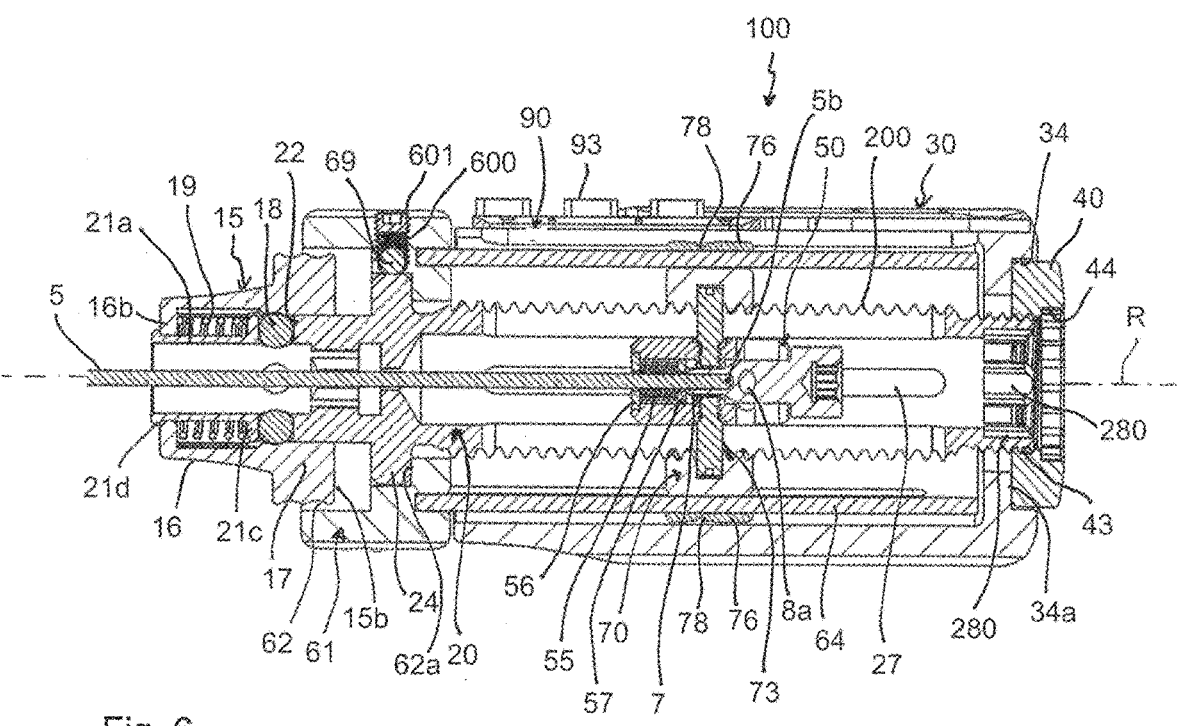
FIG. 6 shows a cross-sectional view of the instrument of FIGS. 4 and 5, with a needle inserted therein, the cross-section taken in a plane including an axis of rotation of a handle portion and an actuator of the instrument, wherein a needle holder is in an intermediate position.

Referring further to FIGS. 4 to 6, the instrument 100 can be coupled via a coupling portion 15 to the shank inserter 10, and more specifically, to the drive shaft of the shank inserter 10. The coupling portion may optionally be part of the instrument. The instrument 100 includes a hollow shaft 20 that is configured to be connected via the coupling portion 15 to the drive shaft of the shank inserter 10, and that is further configured to be connected to a handle portion 30. The handle portion 30 can be rotated by a user, whereby the torque is transmitted to the hollow shaft 20 and the drive shaft of the shank inserter 10. A fixation member 40 may be used to connect the hollow shaft 20 with the handle portion 30 in a rotationally and translationally fixed manner. Moreover, the hollow shaft 20 is housed at least partially in a cavity of the handle portion 30. A needle holder 50 is adapted to be arranged in the hollow shaft 20. The needle holder 50 can be translated within the hollow shaft 20 via an actuating mechanism to permit a tip 6 of the needle 4 to be advanced and retracted relative to the tip 3 of the shank 2 of the bone anchor 1.

The actuating mechanism includes an actuator 60 and a transmission member 70. The actuator 60 is rotatable relative to the hollow shaft 20 and the drive shaft of the shank inserter 10. The transmission member 70 is guided by the actuator 60 in a manner such that when the actuator 60 is rotated, the transmission member 70 follows the rotational movement of the actuator and, at the same time, advances axially relative to the hollow shaft 20. In addition, the transmission member 70 is connected to the needle holder 50 in a manner such that the needle holder 50 follows the axial advancement of the transmission member 70. Thus, the transmission member 70 is configured to convert a rotational movement of the actuator 60 into a translational movement of the needle holder 50. By means of this, the needle 4 can be advanced and retracted relative to the bone anchor 1 independently from a position of the bone anchor 1. An axis of rotation R of the instrument 100, which is also a central longitudinal axis of the instrument, is coaxial with the axis of rotation of the shank inserter 10 and the screw axis of the bone anchor 1.

The parts of the instrument 100 will now be explained in greater detail. Referring additionally to FIGS. 9 to 11, the hollow shaft 20 is an elongate, substantially cylindrical part which has a front end 20a and a rear end 20b. The front end 20a faces towards the shank inserter 10 when the instrument is mounted to the shank inserter. Moreover, the hollow shaft 20 defines a channel extending through the hollow shaft from the front end to the rear end, such that the needle 4 can extend fully therethrough. The channel has various sections described hereinafter. Adjacent to the front end 20a, there is a connection portion 21 for connecting the hollow shaft 20 to the coupling portion 15. The connection portion includes, at the front end 20a, a hollow cylindrical section 21a with an outer diameter such that the cylindrical section 21a is configured to be received in the coupling portion 15, and with an inner diameter sized to receive a portion of the drive shaft. Adjacent to the cylindrical section 21a, there is a section 21b with a greater outer diameter so that a step 21c is formed therebetween. The step 21c may serve as an abutment for a spring of the connection portion 15 (see FIGS. 6 to 8). Another abutment for an end surface of the coupling portion 15 may be formed by a small outwardly extending annular protrusion 21d adjacent to the front end 20a. The section 21b has, close to the step 21c, several equidistantly distributed circumferential compartments 22 for engagement members, such as balls 18, that are configured to engage a groove of the drive shaft to hold an axial position of the drive shaft while allowing rotation of the drive shaft. At a side of the compartments 22 positioned closer to the rear end 20b, a receiving section 23 for receiving the connection portion of the drive shaft is formed, that has an inner contour matching the outer contour of the connection section, to provide a form-fit connection between the drive shaft and the hollow shaft 20. Preferably, the receiving section 23 has a standard connection contour, such as a quarter inch female square contour. At a distance from the step 21c, a circumferential flange or annular projection 24 may be provided that is configured to cooperate with a portion of the actuator 60. A plurality of axial grooves 24a are equidistantly formed in the outer surface of the projection 24, which are adapted to be engaged by balls of the actuator 60. Adjacent to the receiving section 23 towards the rear end 20b, a narrowed section 25 of the channel may have a width that is only slightly greater than an outer diameter of the needle 4. This may provide guidance for the needle 4 once the needle extends through the hollow shaft 20.

Figure 7:
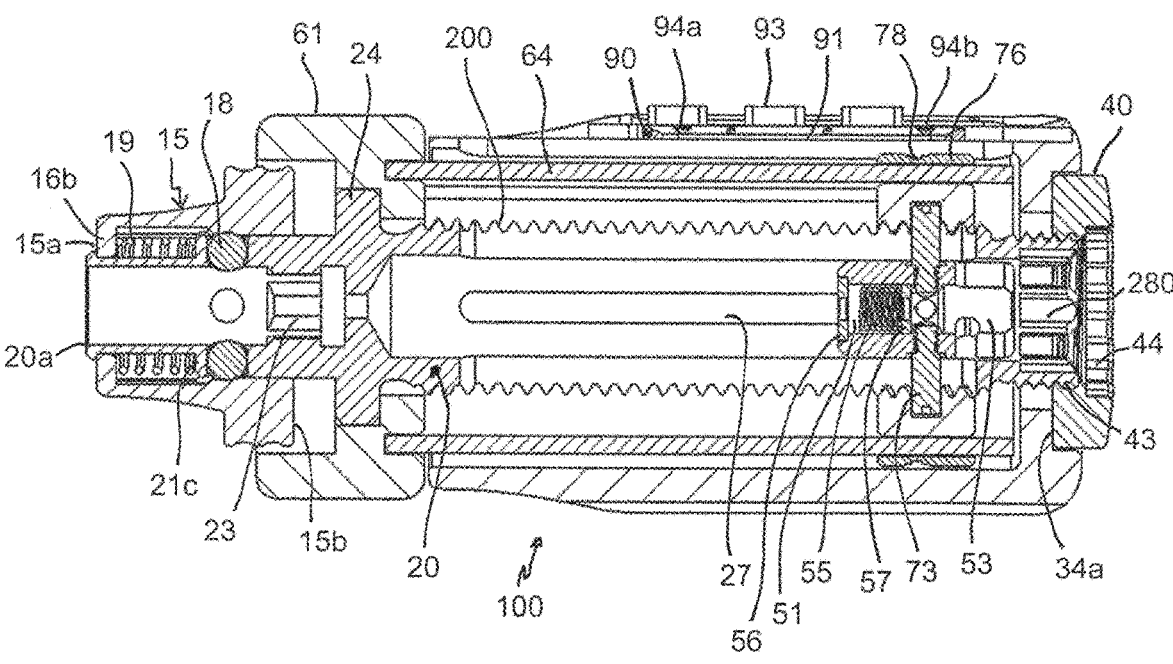
FIG. 7 shows a cross-sectional view of the instrument of FIGS. 4 to 6 without the needle, and wherein the needle holder is in a retracted or rearmost position.
Figure 8:
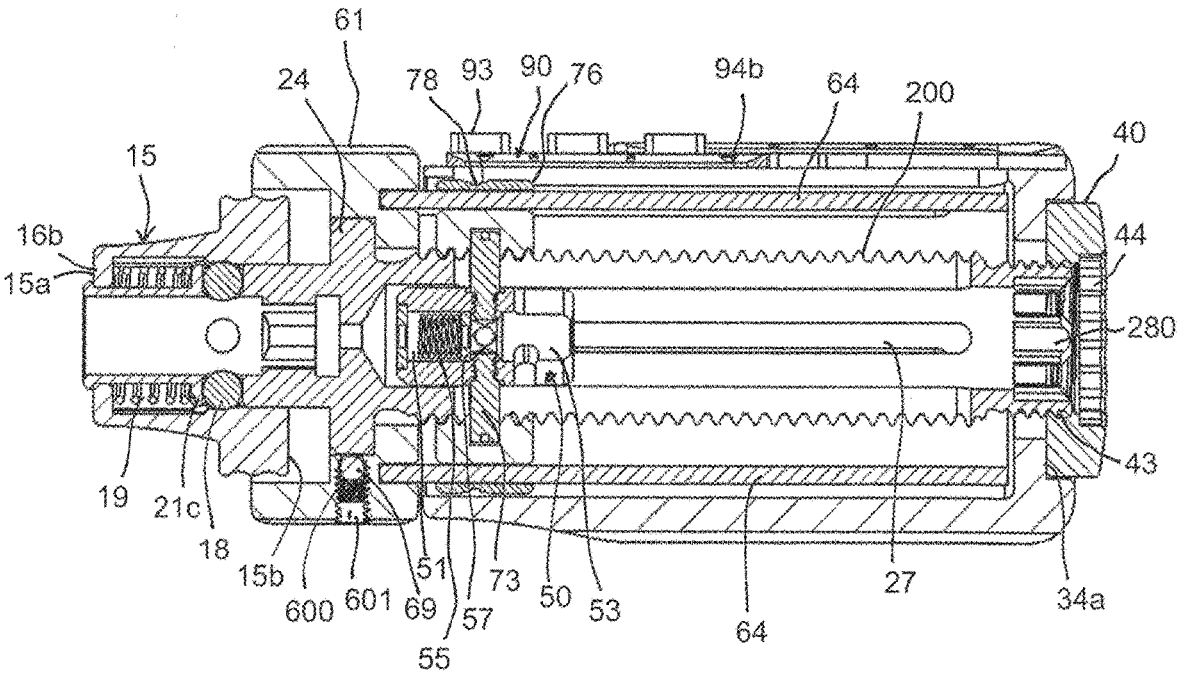
FIG. 8 shows a cross-sectional view of the instrument of FIGS. 4 to 7, wherein the needle holder is in an advanced or foremost position.

The channel then widens towards the rear end 20b into a needle holder receiving section 26, which serves for receiving the needle holder 50 therein. The needle holder receiving section 26 has a length such that the needle holder 50 can move therein in an axial direction along a defined length. At least one, preferably four, axially elongate slots 27 that are closed at both ends are formed in the wall of the hollow shaft 20 equidistantly in the circumferential direction. The slots 27 permit pins 73 to extend therethrough for holding the needle holder 50, as described in greater detail below. When the pins 73 abut against or are close to the rear end of the slots 27 that are located closer to the rear end 20b of the hollow shaft 20, respectively, the needle holder 50 is in a rearmost position (FIG. 7). When the pins 73 abut against or are close to the opposite front end of the slots 27, respectively, the needle holder 50 is at a foremost position (FIG. 8).

Between the annular projection 24 and a position at a distance from the rear end 20b, the outer surface of the hollow shaft 20 includes an advancement structure, which in this embodiment is a thread 200. The thread 200 is configured to cooperate with an advancement structure provided on the transmission member 70 to facilitate an axial advancement of the transmission member 70 along the outer surface of the hollow shaft 20. The outer diameter of this threaded section of the hollow shaft 20 may be smaller than that of the annular projection 24. The type of thread depends on the application and the desired dependency between the action of the actuator 60 and the advancement of the needle holder 50. Thus, the pitch, the threadform, and the number of thread entries may be selected accordingly. A multiple thread may be used for obtaining a greater advancement of the needle. In the embodiment, a thread with three entries is used. However, a single thread, a double thread, or any other multiple thread may also be applied.

Adjacent to the rear end 20b, a reduced outer diameter section 28 with an external thread is formed that is configured to cooperate with an internal thread in a bore of the fixation member 40 (FIGS. 4 and 6 to 8). In addition, a plurality, more specifically four, axial slots 29 extend through the end portion with the outer thread. Thereby, posts 280 are formed that are configured to extend through corresponding recesses in the handle portion 30 to provide a form-fit connection between the hollow shaft 20 and the handle portion 30. In this manner, rotation of the hollow shaft 20 relative to the handle portion 30 is prevented when the fixation member 40 is screwed onto the posts 280 of the hollow shaft 20. It shall be noted that other rotation preventing structures between the hollow shaft 20 and the handle portion 30 may also be envisaged.

In the following, the coupling portion 15 which couples the hollow shaft 20 to the drive shaft will be described in greater detail. The coupling portion 15 is exemplary and any outer suitable coupling can also be used. As best seen in FIGS. 4 to 8, the coupling portion 15 is a sleeve-like part and is configured to receive a portion of the hollow shaft 20 therein. The coupling portion 15 has a front section 16 adjacent to a front end 15a and a rear section 17 adjacent to a rear end 15b. The rear section 17 has an inner diameter such that the rear section fits tightly around the lager diameter section 21b of the hollow shaft and an outer diameter that allows the rear section 17 to protrude into a portion of the actuator 60. The front section 16 extends around the cylindrical section 21a of the hollow shaft 20. Moreover, the front section 16 is flexible, for example, by means of axial slits 16a, as best seen in FIG. 5, that are open to the front end 15a. The slits 16a and an inner annular projection 16b at the front end enable the front section 16 of the coupling portion 15 to be snapped over the portion 21a of the hollow shaft 20 and to abut against the annular projection 21d adjacent to the front end 20a of the hollow shaft 20. In the front section 16, a compartment is formed in which a helical spring 19 is accommodated. The helical spring 19 extends around the portion 21a of the hollow shaft 20 and abuts against the step 21c. By means of this, the hollow shaft 20 is biased against the annular projection 16b of the coupling portion 15, so that the two parts are firmly connected. At a distance from the front end 15a, the balls 18 are placed into the compartments 22 of the hollow shaft 20 and extend radially inwardly to some extent to permit rotation of the hollow shaft 20.

Figure 12:
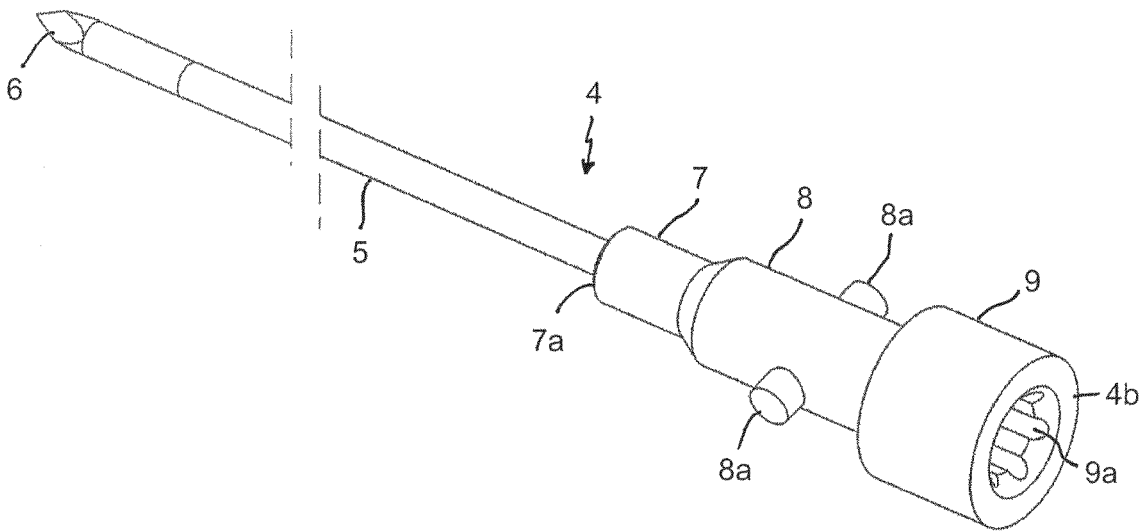
FIG. 12 shows an enlarged perspective view from a rear end of a needle to be used with the instrument of FIGS. 4 to 8.
Figure 13:
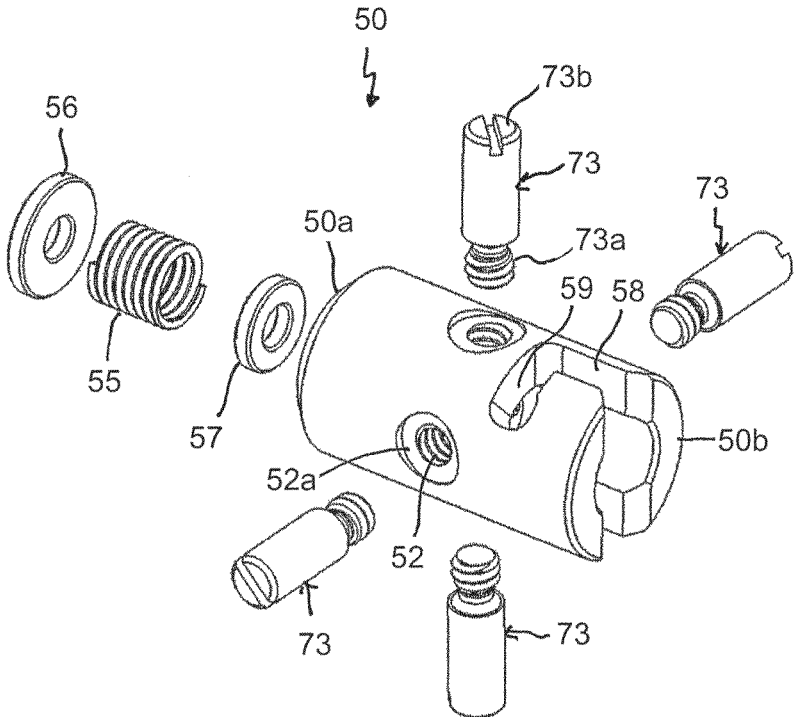
FIG. 13 shows a perspective exploded view of the needle holder of the instrument of FIGS. 4 to 8.

Referring to FIGS. 12 and 13, the needle 4 and the needle holder 50 will now be described in greater detail. As depicted in FIG. 12, the needle 4 includes a thin rod portion 5 with a tip 6 at its front end. The tip 6 preferably is a sharp tip that is suitable for forming a hole in bone. At the side opposite to the tip 6, a holding portion is provided that includes a cylindrical front portion 7, an intermediate thicker portion 8, and a head portion 9 at a rear end 4b. Preferably, the rod portion 5 and the holding portion are separate parts. A rear end 5b (FIG. 6) of the rod portion 5 may be mounted to the cylindrical front portion 7 of the holding portion, for example, press-fit into a bore of the cylindrical front portion 7, so that between the rod portion 5 and the cylindrical front portion 7, a small shoulder 7a is formed. At the outer surface of the intermediate portion 8, two projections 8a, preferably cylindrical projections, extend outward in opposite directions. The projections 8a serve for mounting the needle 4 to the needle holder 50. The head portion 9 has an engagement portion 9a for a tool at its free end. With the tool, such as a driver, the needle 4 can be pushed and rotated to mount and release the needle from the needle holder 50. It shall be noted that the needle can be any suitable needle, such as a Jamshidi needle or a needle having a special tip, such as a tip provided with a sensor.

As shown in FIGS. 6 to 8 and 13, The needle holder 50 is a substantially cylindrical part with a front end 50a and a rear end 50b. The needle holder defines a channel extending completely through the needle holder from the front end 50a to the rear end 50b, such that the tip 6 of the needle 4 can be inserted from the rear end 50b and can extend with the rod portion 5 all the way through the needle holder 50. Adjacent to the front end 50a, the channel has a front section 51 with an inner diameter large enough to guide the rod portion 5 of the needle 4 therethrough and to further house a biasing member for holding the needle in the needle holder. At a distance from the front end 50a, four threaded radially extending through holes 52 are formed equidistantly in the circumferential direction in the wall of the needle holder 50. The through holes 52 are configured to receive the connection pins 73 (see also FIGS. 4 and 6 to 8) therein to connect the transmission member 70 to the needle holder 50. Each connection pin 73 has a threaded front portion 73a that is configured to engage a corresponding one of the threaded holes 52 in the needle holder 50. Opposite to the front portion 73a, the connection pins 73 have a rear end 73b with an engagement structure, such as a slit or a polygonal recess, for screwing in the pin. The threaded front portion 73a has a smaller outer diameter than the remaining pin, and a length such that the connection pin 73 can be inserted into the needle holder 50 only to a depth such that the needle 4 inside the needle holder is not touched by the connection pins 73. To limit the insertion, a counterbore 52a at the entrance of the threaded through hole 52 may be provided against which a portion of the pin 73 abuts. Adjacent to the rear end 50b, a rear section 53 for the intermediate portion 8 of the needle 4 is provided. In the front portion 51 of the channel, a helical spring 55 is housed between a washer 56 that is fixed to the front end 50a and configured to permit the rod portion 5 of the needle to pass therethrough and a movable washer 57 against which the shoulder 7a of the needle 4 is configured to abut.

At the rear end 50b, two axially extending recesses 58 that are offset by 180° from each other are formed in the wall of the needle holder 50, that permit the projections 8a of the intermediate portion 8 of the needle 4 to be guided therethrough when the needle 4 is inserted. At a distance from the rear end 50b, the recesses 58 continue into end portions 59 which extend in the circumferential direction, and thus are transverse to the axial portion of recesses 58. The end portions 59 extend circumferentially in a same rotational direction, so that when the projections 8a of the needle 4 reach the end portions during insertion of the needle, rotation in one direction moves the projections into the end portions 59 of the recesses 58, respectively, and rotation in the other direction moves the projections out of the end portions.

Figure 14:
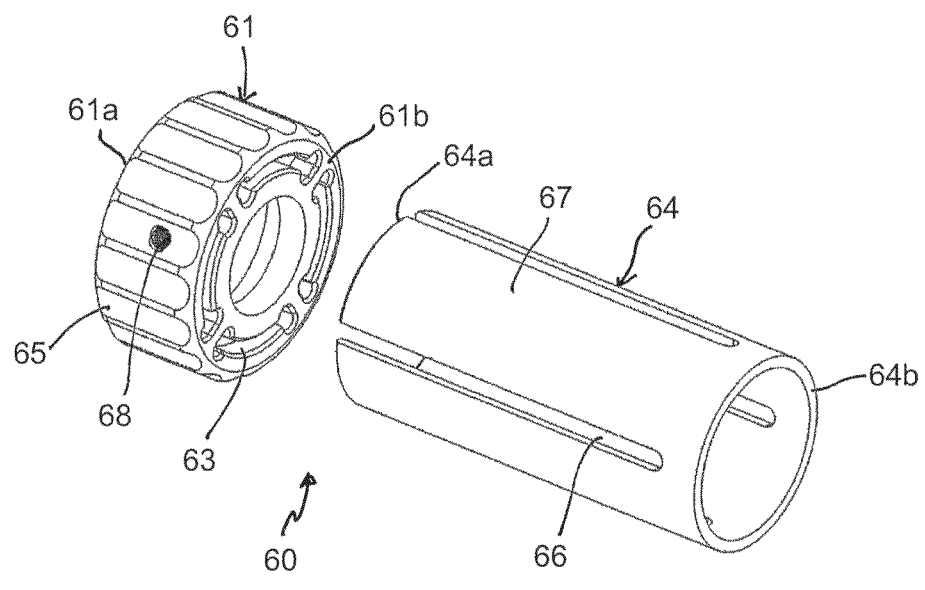
FIG. 14 shows a perspective exploded view of the actuator of the instrument of FIGS. 4 to 8 for actuating the movement of the needle holder.

Referring to FIGS. 14 and 4 as well as FIGS. 6 to 8, the actuator 60 will be described. The actuator 60 includes a sleeve-shaped actuator wheel 61 that has a front end 61a and a rear end 61b, wherein in the mounted state, the front end 61a faces the connection portion 15. At the front end 61a, a coaxial recess 62 may be formed that is configured to receive a portion of the rear end 17 of the connection portion 15. Following the recess 62, the inner diameter of the sleeve is such that the annular projection 24 of the hollow shaft 20 fits therein and abuts in the axial direction against a step 62a. Between the step 62a and the rear end 61b, the inner diameter of the sleeve is such that the threaded portion of the hollow shaft 20 can pass and extend therethrough. In the free end surface of the rear end 61b, a plurality, in the embodiment four, equidistantly arranged circumferentially extending slits 63 are formed that serve for receiving portions of an actuator tube 64 therein, for example, in a press-fit manner. The slits 63 may have enlarged end portions on both ends, respectively, for facilitating mounting of the actuator tube 64. The outer surface of the actuator wheel 61 includes a gripping structure 65 which may include axially extending depressions or grooves that facilitate gripping and rotating the actuator wheel 61.

The actuator tube 64 has a front end 64a and a rear end 64b, and a plurality of axially extending slits 66, in the embodiment four slits. The slits 66 are open towards the front end 64a and closed towards the rear end 64b, so that four tube sections 67 are formed. The tube sections 67 are mounted with the front end 64a into the recesses 63 of the actuator wheel 61. Thereby, the actuator tube 64 protrudes from the rear end 61b of the actuator wheel 61, with a smaller diameter compared to that of the actuator wheel. The length of the actuator tube 64 is such that in the mounted state, the rear end 64b of the actuator tube extends up to a small distance from the rear wall of the handle portion 30. When the actuator is mounted to the hollow shaft 20, the mounting pins 75 that connect the ring 76 with the transmission member 70 can extend through the slits 66, respectively.

The actuator 60 may be mounted to the hollow shaft 20 via a spring biased rotatable connection. As shown in particular in FIGS. 4 and 6, at an axial position corresponding to the position of the annular protrusion 24 of the hollow shaft 20, the actuator wheel 61 defines a plurality of equidistantly arranged threaded through holes 68, in the embodiment three through holes. Balls 69 are arranged in the through holes 68 and are pressed via helical springs 600 by the action of set screws 601 against the surface of the protrusion 24 of the hollow shaft 20. The grooves 24 a provide resting positions that can be engaged by the balls 69 incrementally when rotating the actuator wheel 61. In other words, when rotating the actuator wheel 61, the balls 69 can move out of each of the grooves 24a and snap into circumferentially neighboring grooves 24a. Thus, a haptic feedback may be given to a user when the actuator wheel is rotated. The actuator wheel 61 is prevented from axial movement since the actuator wheel is connected via the actuator tube 64 to the transmission member 70 and the needle holder 50.

Figure 15:
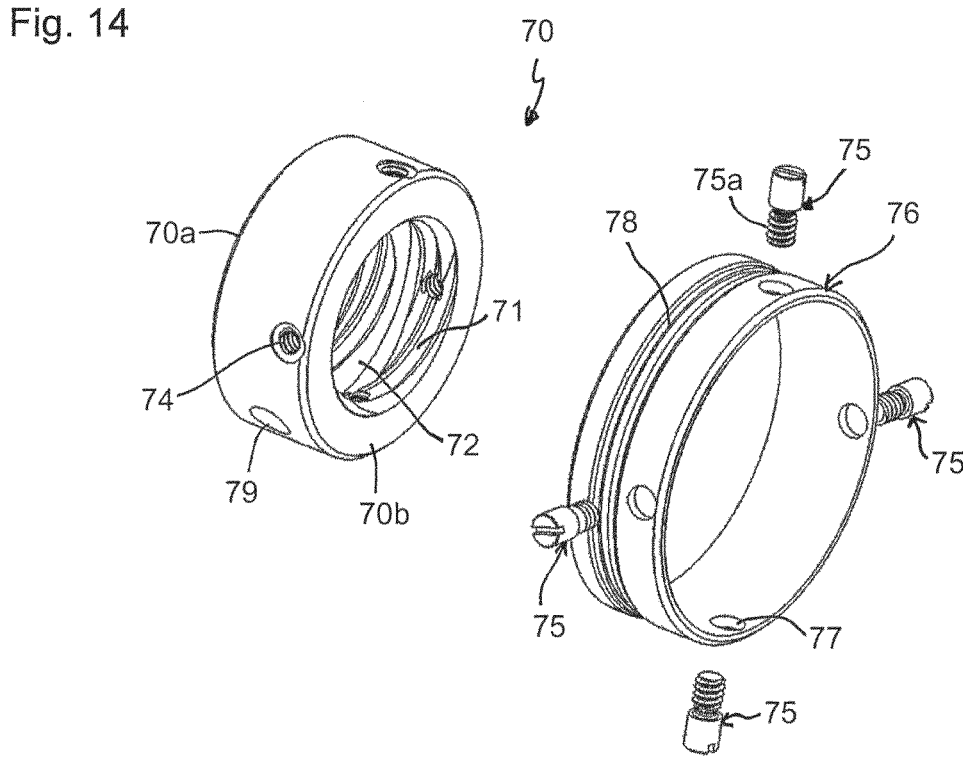
FIG. 15 shows a perspective exploded view of a transmission member of the instrument of FIGS. 4 to 8 for transmitting the movement of the actuator to the needle holder, and of a needle position indication device in the form of a ring.
Figures 16, 17:
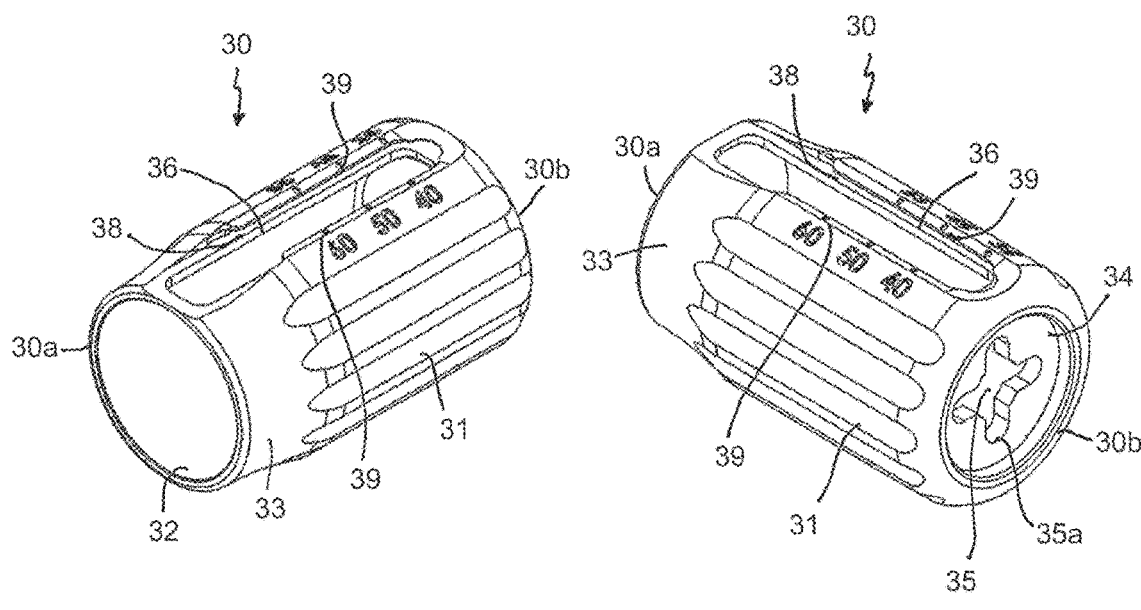
FIG. 16 shows a perspective view from a front end of the handle portion of the instrument of FIGS. 4 to 8.
FIG. 17 shows a perspective view from a rear end of the handle portion of FIG. 16.
Figures 18, 19:
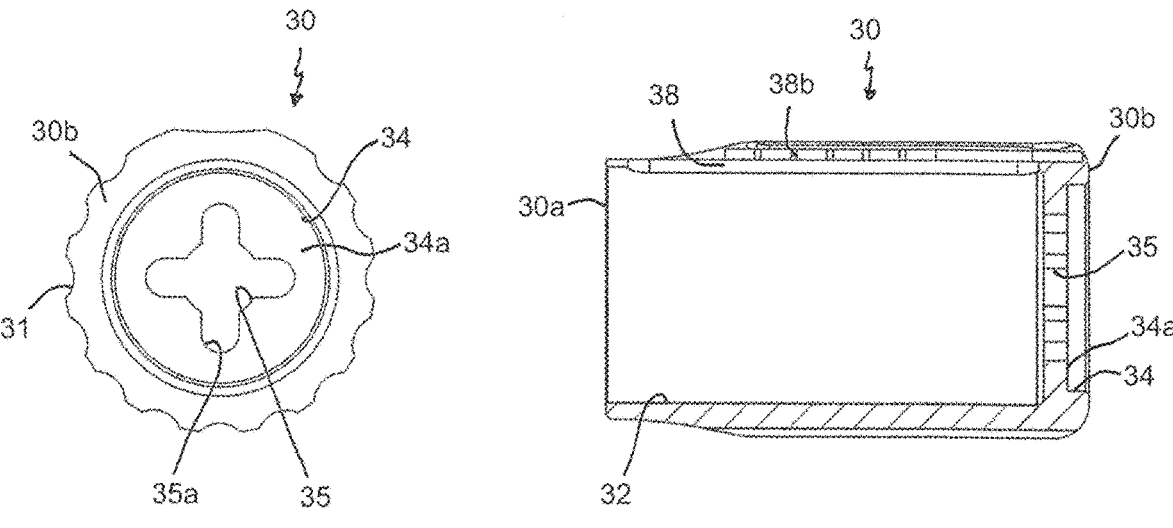
FIG. 18 shows a rear view of the handle portion of FIGS. 16 and 17.
FIG. 19 shows a cross-sectional view of the handle portion of FIGS. 16 to 18, the cross-section taken in a plane including an axis of rotation of the handle portion.

The transmission member is shown in greater detail in FIG. 15. The transmission member 70 is a sleeve-like part with a front end 70a and a rear end 70b. An internal thread 71 configured to cooperate with the external thread 200 on the hollow shaft 20 is formed on the inner wall of the sleeve to allow the transmission member 70 to move back and forth on the hollow shaft 20 in the axial direction. The advancement structure in the form of the thread 71 on the transmission member 70 and the advancement structure in the form of the thread 200 on the hollow shaft 20 may be configured such that the distance per revolution which the transmission member 70 moves axially corresponds to the distance the shank 2 is advanced per revolution of the drive shaft.

The transmission member 70 is connected to the needle holder 50 via the connection pins 73 as shown in FIGS. 6 to 8, so that when the transmission member 70 moves along the hollow shaft 20 in the axial direction, the needle holder 50 within the hollow shaft 20 moves together with the transmission member 70 in the axial direction. The connection pins 73, in the embodiment four pins, extend radially through the slots 27 of the hollow shaft 20, respectively. The rear ends 73b of the connection pins extend into a circumferential groove 72 formed in the inner wall of the transmission member 70. Thus, when the transmission member 70 advances along the threaded hollow shaft 20, the rear ends 73b of the connection pins 73 can rotate in the groove 72 of the transmission member 70. The pins 73 can be inserted through a mounting hole 79 that extends through the transmission member into the groove 72.

At an axial position between the rear end 70b and the groove 72, a plurality, in the embodiment four, equidistantly arranged threaded through holes 74 are formed that serve for receiving mounting pins 75 for mounting a needle position indication device in the form of a ring or sleeve 76 to the transmission member 70. The ring 76 has substantially the same axial length and an inner diameter that permits mounting around the tube portion 64 of the actuator 60. The inner wall of the ring 76 is threadless, so that the ring 76 can slide along the tube portion 64. At positions corresponding to the threaded through holes 74 in the transmission member 70, the ring 76 defines unthreaded holes 77 which permit only a threaded front portion 75a of the mounting pins 75 to extend therethrough and engage the threaded holes 74 of the transmission member 70. It shall be noted that the ring 76 is thinner in the radial direction compared to the transmission member 70, since the ring 76 has to fit into the space between the actuator and the handle portion in the radial direction. In the outer surface of the ring 76, a circumferential indication mark 78 is provided which may be, for example, a groove, that may be provided with a coloring and/or a colored ring. Hence, when the transmission member 70 moves, the ring 76 with the indication mark 78 moves in the same way, for example, a same axial distance. Therefore, the indication mark 78 is configured to display the axial position of the needle holder 50, and therefore the axial position of the tip 6 of the needle relative to the tip 3 of the bone anchor 1. For this purpose, there is a window in the handle portion 30, as explained in greater detail below.

Turning now in addition to FIGS. 16 to 19, the handle portion 30 will be described in greater detail. The handle portion 30 may be an elongate, substantially cylindrical part that has a front end 30a and a rear end 30b. An outer surface portion 31 that extends from a position close to the rear end 30b to a distance from the front end 30a includes a gripping structure such as, for example, axial grooves. Between the outer surface portion 31 with the gripping structure and the front end 30a, the outer diameter of the handle portion may include a tapered portion 33 that tapers and narrows towards the front end 30a, so that the outer diameter of the handle portion 30 close to the actuator wheel 61 is smaller or has the same size as that of the actuator wheel 61. The handle portion 30 further defines an elongate passage in the form of a cylindrical bore 32 extending from the front end 30a to a distance from the rear end 30b. The diameter of the bore 32 is such that, in the radial direction, the hollow shaft 20, the actuator tube 64, the transmission member 70 and the ring 76 can extend therein.

Adjacent to the rear end 30b, a cylindrical recess 34 with a bottom 34a is formed that is sized to receive a portion of the fixation member 40 (see FIGS. 6 to 8). A coaxial opening 35 with a reduced inner diameter compared to the diameter of the bore 32 is provided in the bottom 34a of the recess 34. The opening 35 has four rounded side recesses 35a offset from each other by 90° that are configured to receive the posts 280 of the hollow shaft 20, in order to connect the hollow shaft 20 and the handle portion 30 to each other in a rotationally secured manner. The posts 280 can pass through the side recesses 35a, respectively, so that free ends of the projections 280 project out therefrom.

In addition, a window 36 is provided in the handle portion 30 that exposes a portion of the inside of the handle portion. More specifically, the window 36 exposes at least a portion of the ring 76 with the marking 78. Thus, the marking 78 that is indicative of the position of the needle holder 50 can be used for adjusting the position of the needle holder 50, and thus the position of the needle 4. The window 36 may have a rectangular shape with rounded edges, with a length that is greater than a difference between lengths of the longest and the shortest shanks of bone anchors that can be used, plus the length that the needle 4 is allowed to move. A groove 38 is formed in the wall of the handle portion 30 for receiving a shank length indication device in the form of a slide 90 that is configured to indicate the possible travel path of the needle holder 50 and which serves for setting a shank length of the bone anchor that is actually being used. The groove 38 has a substantially rectangular contour and a flat bottom. At the tapered portion 33 of the handle 30, the height of outer wall of the groove decreases towards the front end 30a, such that a portion of the bottom is free which permits the slide 90 to enter the groove 38 easily. Inside the groove 38 there are protrusions 38b along at least a portion of the length of the window for cooperating with the slide 90. At the outer wall of the handle portion 30, around the window 36, are markings 39 that are configured to indicate the length of the shank of the bone anchor that is being used. In the embodiment, the length is indicated in increments wherein, for example, even numbers are indicated at one side of the window and odd numbers are indicated at the opposite side of the window. For example, if the smallest length of a shank that can be used is 35 mm and a greatest length of a shank that can be used is 60 mm, the even numbers between 40 mm and 60 mm with an increment of 10 mm are indicated on one side of the window 36 and the odd numbers between 35 mm and 55 mm are indicated on the opposite side of the window. The markings 39 are arranged such that the smallest length is displayed closer to the rear end 30b of the handle portion 30, and the displayed lengths increase towards the front end 30a.

As shown in FIGS. 20 to 22, the slide 90 includes a substantially rectangular flat plate that is configured to be slid into the groove 38 and that can be moved therein in an axial direction, i.e., along a length axis of the plate that is parallel to the longitudinal axis of the handle portion 30. The slide 90 has a front end 90a and a rear end 90b, wherein the front end is positioned closer to the actuator wheel 61 in the assembled state when the slide 90 is in the groove 38. A longitudinal slot 91 is formed in the middle of the slide in the transverse direction which may extend almost along the whole length of the slide 90. The slot 91 is configured to display a portion of the actuator tube 64 and the ring 76 with the marking 78 that are visible through the window 36 of the handle portion 30. Hence the slide also forms a needle position indication device. A countersink 92 around the slot 91 may improve the visibility of the ring 76 and may carry markings. On the upper side of the slide that faces outward, a plurality of elongate gripping protrusions 93 may be formed that may be arranged along both long sides of slot 91 to allow gripping of the slide 90 and sliding of the slide in the groove 38.

On the surface of the countersink 92, markings are provided that can be aligned with the markings 39 on the handle portion 30 when the slide 90 is moved. In greater detail, close to the rear end 90b, a first type of marking 94b may be provided that is configured to be aligned with one of the markings 39 around the window 36 that indicate possible shank lengths. The first type of marking can be, for example, two arrows pointing to the center of the slot 91 in the circumferential direction of the handle portion 30, such that, when the slide 90 is at a position in which the two arrows are aligned with a marking 39 on the handle portion 30, the marking 94b indicates the length of a shank of an inserted bone anchor 1. This first type of marking 94b may have a color, for example, green. Moreover, a second type of marking 94a may be provided close to the front end 90a of the slide 90. This second type of marking 94a may indicate the maximum admissible projection of the needle 4 out of the shank 2. In other words, the second type of marking indicates the maximum admissible or desirable travel path of the needle holder 50 to ensure the maximum admissible projection of the needle. The marking 94a may also include two arrows that point with their tips towards each other. A color of the second type of marking may be red, for example, to indicate the limit of the admissible advancement of the needle 4. In between the first and the second type of markings, there may be a third type of marking 94c that may include equidistantly spaced apart dashes and/or dots on each side of the slot 91, wherein the markings 94c are offset from each other on one side relative to the other side. The markings 94c may indicate the advancement of the needle in increments.

Generally, the markings 39 on the handle portion 30 provide a first scale indicative of possible lengths of the shank of a bone anchor 1, while the markings on the slide 90 provide a second scale indicative of the possible positions of the tip 6 of the needle with respect to the tip of the bone anchor 1. Lastly, the slide 90 defines on each of the long sides, at approximately the middle of the long sides, recesses, for example, two V-shaped recesses 95 in the outer edge of the slide. The recesses 95 are configured to cooperate with the protrusions 38b inside the groove 38. Thereby, the adjustment of the markings on the slide 90 relative to the markings 39 on the handle portion 30 may be more easily facilitated, and the slide may be held at specific positions.

As further depicted in FIGS. 6 to 8, the fixation member 40 fits at least partially in the recess 34 at the rear end 30b of the handle portion 30. The fixation member defines a threaded bore 43 that is configured to be screwed onto the posts 280 of the hollow shaft 20. On the side of the fixation member opposite the rear end 30b of the handle portion 30, the fixation member defines a tool engagement recess 44 for screwing the fixation member 40 onto the posts 280 of the hollow shaft 20. The inner space between the posts 280 of the hollow shaft 20 is such that the needle holder 50 can extend therein and the threaded bore 43 has a size such that insertion and/or removal of the needle 4 through the fixation member 40 is possible. The fixation member 40 is configured to abut against the bottom 34a of the recess 34 in the handle portion 30 (FIGS. 7 and 8).

The parts and portions of the instrument and/or the bone anchor insertion device, the bone anchor, and/or the needle may be made of any material, preferably, however, of a bio-compatible material, such as titanium or stainless steel, or any other bio-compatible metal or metal alloy, or plastic material. For bio-compatible alloys, a NiTi-alloy, for example Nitinol, may be used. Other materials that can be used are, for example, Magnesium or Magnesium alloys, or bio-compatible plastic materials that can be used may be, for example, Polyether ether ketone (PEEK) or Poly-L-lactide acid (PLLA). The parts can be made of the same or of different materials from one another. For the instrument, a material that is easy to clean may be preferred.

The needle holder 50, the hollow shaft 20, the transmission member 70 with the ring 76, the handle portion 30 with the slide 90, and the actuator 60 are usually preassembled such that their respective front ends face in the direction of the connection portion 15. When the needle holder 50 is placed into the hollow shaft 20, the transmission member 70 is screwed onto the hollow shaft 20 from the rear end thereof, and the pins 73 are inserted through the mounting hole 79, passed through the slots 27 of the hollow shaft 20 and screwed into the threaded holes 52 of the needle holder 50. The actuator 60 is placed with the actuator wheel 61 around the hollow shaft 20 and the set screws 601 are tightened. The ring 76 is mounted around the actuator tube 64 and fixed with the mounting pins 75 to the transmission member 70, and the actuator tube 64 is mounted to the actuator wheel 61. After that, the hollow shaft 20 is fixed to the handle portion 30 via the fixation member 40 that is screwed onto the threaded posts 280 of the hollow shaft 20. Tightening the fixation member 40 firmly fixes the hollow shaft 20 to the handle 30 so that rotation of the handle 30 also rotates the hollow shaft 20. The actuator 60 remains rotatable with respect to the hollow shaft 20 and with respect to the handle portion 30.

To use the instrument 100 with a shank inserter 10, the optional coupling portion 15 is mounted to the connection portion 21 of the hollow shaft 20. The instrument 100 preassembled in this manner can be connected to a shank inserter 10. To accomplish this, the connection portion of the drive shaft is inserted into the connection portion 21 of the hollow shaft until the connection portion of the drive shaft is received in the receiving section 23, so that the form-fit engagement allows transmission of torque to the drive shaft. The shank inserter may be already connected to a bone anchor 1 to be inserted into bone, or the bone anchor 1 can be fixed to the shank inserter 10 when the shank inserter has already been connected to the instrument 100.

In operation, when the actuator wheel 61 is rotated, the rotational movement of the actuator tube 64 forces the transmission member 70 to travel in an axial direction via the engagement of the thread 71 of the transmission member 70 with the thread 200 of the hollow shaft 20. Since the transmission member 70 is connected via the pins 73 to the needle holder 50, the needle holder 50 will travel axially together with the transmission member 70.

The needle 4 can be inserted and removed by means of a push and turn action as follows. When the projections 8a are received in the end portions 59, the needle 4 is secured against inadvertent removal from the needle holder 50. When the shoulder 7a of the holding portion of the needle 4 abuts against the washer 57, the spring 55 urges the washer against the shoulder 7a, so that the needle 4 as a whole is biased towards the rear end 50b of the needle holder 50. Thereby, the projections 8a are held in the transverse end portions 59 of the axial recesses 58. Removal of the needle 4 is effected by pushing the holding portion of the needle against the washer 57, which frees the projections 8a so that they can be moved out of the transverse end portions 59 by rotating the needle in a counter or opposite direction compared to when the needle is attached to the needle holder. For example, in the embodiment, the end portions 59 extend in the counterclockwise direction when viewed from the read end 50b, so that pushing and rotating the needle in the counterclockwise direction locks the needle 4 in the needle holder 50, while pushing and rotating the needle in the clockwise direction releases the needle 4 from the needle holder 50. This push and turn action allows for a quick and simple mounting and removal of the needle. The rod portion 5 of the needle may be exchanged relative to the holding portion, or the entire rod portion together with the holding portion of the needle 4 can be replaced or exchanged.

Referring to FIGS. 23a to 23d, in clinical use, once a bone anchor with a specific shank length has been selected, the slide 90 is adjusted to the position in which its first type marking 94b is aligned with the marking 39 which corresponds to the shank length of the bone anchor. In the example shown, a bone anchor with a shank length of 60 mm has been selected, and the slide 90 has been adjusted correspondingly.

Once the needle 4 has been inserted and locked in the needle holder 50, the position of the needle is adjusted with the actuator. By rotating the actuator wheel 61, for example, in the clockwise direction, the needle 4 is advanced, and by rotating the actuator wheel, in this example, in the counterclockwise direction, the needle is retracted. During adjustment of the position of the needle 4, the marking 78 on the ring 76 displayed through the window 36 and the slot 91 indicates the position of the tip 6 of the needle 4 relative to the tip 3 of the bone anchor 1.

Figures 23A, 23B, 23C, 23D:
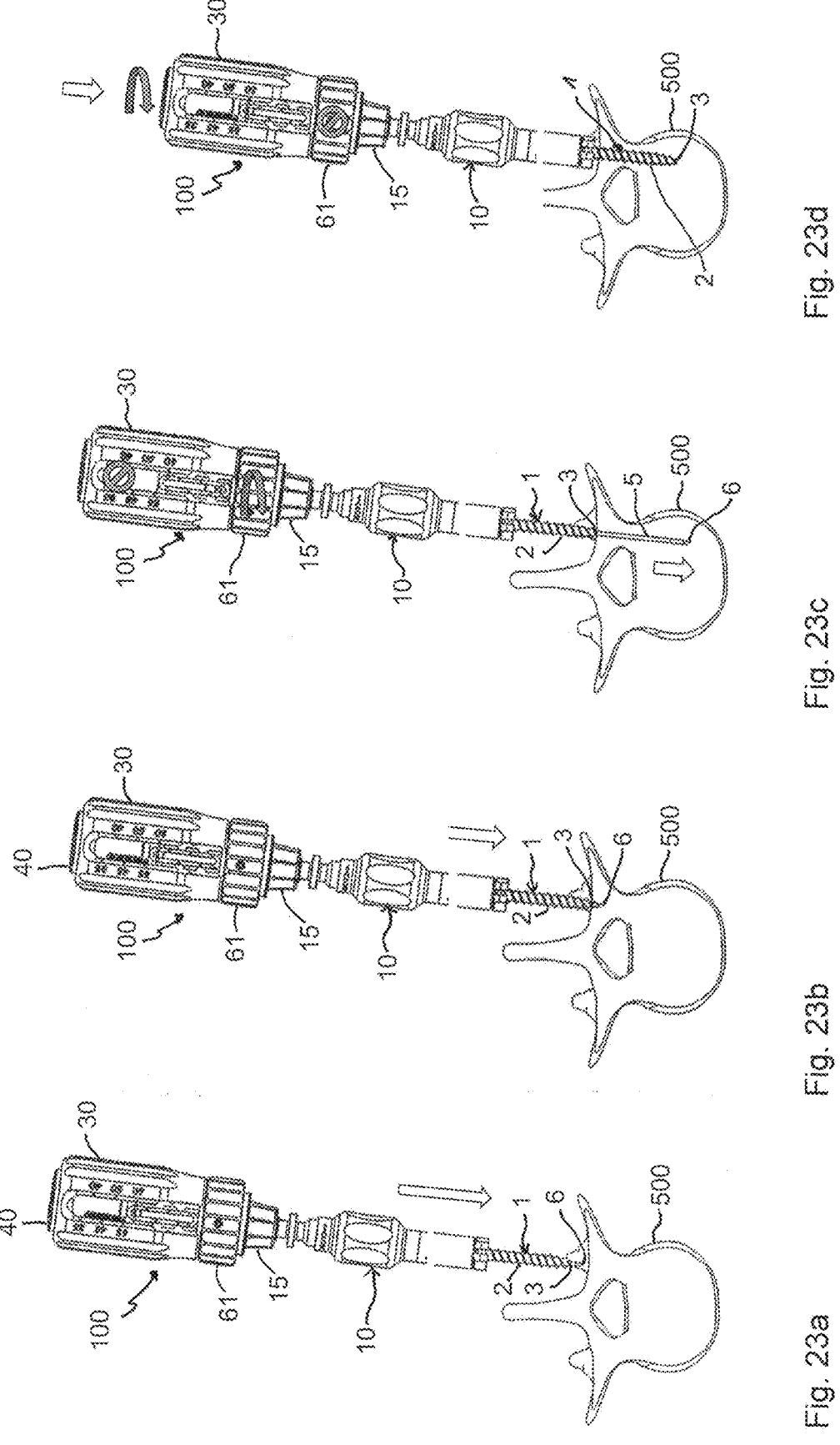
FIGS. 23a to 23d show schematic views of steps for using the instrument together with a shank inserter, a bone anchor, and a needle.

As shown in FIG. 23a, the surgical instrument prepared in this manner is ready to insert the bone anchor 1 into bone, in the example, in a pedicle of a vertebra 500. Next, as shown in FIG. 23b, the bone anchor is placed onto the bone surface and the tip 6 of the needle 4 is hit or otherwise advanced into the bone until the needle 4 has penetrated the cortical bone.

Next, as depicted in FIG. 23c, the handle portion 30 is held stationary and the actuator wheel 61 is rotated in the clockwise direction. Thereby, the needle 4 penetrates deeper into the bone. The distance of travel of the tip 6 of the needle can be seen by the position of the marking 78 of the ring 76 relative to the first type marking 94b.

As further shown in FIG. 23d, once the desired depth has been reached, the actuator wheel 61 of the actuator 60 is held stationary and the handle portion 30 is rotated in the clockwise direction to screw the bone anchor 1 over the needle 4 into the bone. Preferably, the bone anchor 1 is a self-tapping bone anchor that is configured to cut the thread into the bone by itself during rotation.

Finally, the shank inserter 10 can be decoupled from the bone anchor 1 together with the instrument 100 still attached to the shank inserter and with the needle 4 still extending through the entire device. Alternatively, the needle 4 can be removed first, and the shank inserter 10 can then be released from the bone anchor thereafter.

Since the path the needle can travel covers about a length of the shank of a usual bone anchor or more, the instrument 100 and the same needle 4 can be used in connection with different bone anchors having different lengths. The needle position can be monitored during use as it is displayed on the slide 90.

Figure 24:
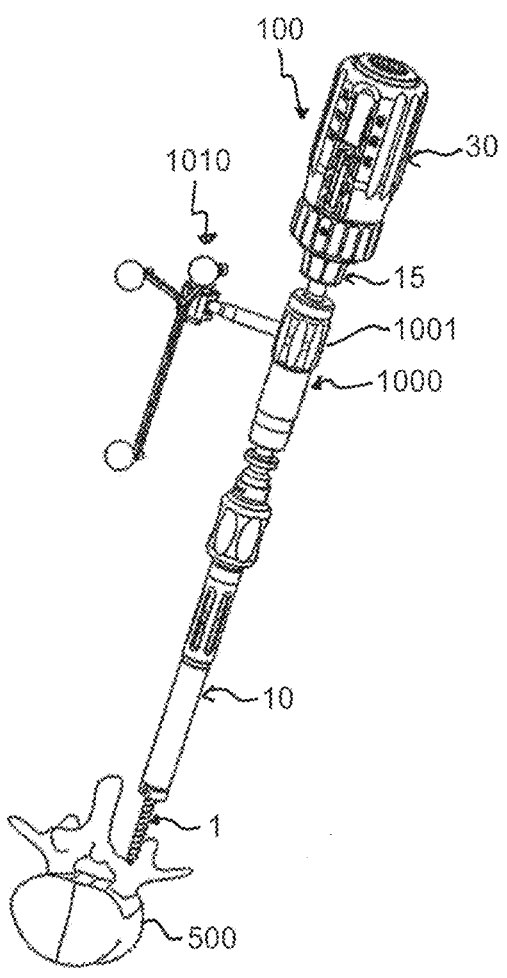
FIG. 24 shows a perspective view of a second embodiment of a surgical instrument which includes the instrument of FIGS. 1 to 23d.

Referring to FIG. 24, a second embodiment of the surgical instrument is shown. Identical or similar parts and portions are indicated with the same reference numerals, and the descriptions thereof will not be repeated. The shank inserter 10 and the instrument 100 are identical to the previous embodiment. However, between the shank inserter 10 and the instrument 100, an adapter 1000 is mounted that has a rear end that is coupled to the hollow shaft 20 in the same manner as the drive shaft of the previous embodiment is coupled to the hollow shaft 20. The adapter 1000 has a front connection portion that is connected to the shank inserter 10. The hollow shaft 20 of the instrument 100 is coupled to an inner shaft (not shown) of the adapter member 1000, which is also coupled to the drive shaft of the shank inserter 10. Thus, torque can be transmitted from the handle portion 30 through the adapter member 1000 to the drive shaft of the shank inserter 10. A secondary instrument 1010, such as a navigation array for optical or any other navigation, can be mounted on the adapter member 1000 via a mounting sleeve 1001. The mounting sleeve 1001 may be, for example, rotatable around the shaft of the adapter member 1000. By means of this, while the torque is transmitted via the handle 30 to the drive shaft, the secondary instrument 1010 can be kept stationary by gripping the secondary instrument 1010 or the mounting sleeve 1001 with the other hand. Thereby, the orientation of the secondary instrument 1010 such as a navigation array can be maintained relative to the rest of the device, e.g., while the rest of the device is rotated. This may be used for surgery under fluoroscopy or with computer-based navigation assisted systems.

It shall be noted that instead of a navigation array, other secondary instruments can also be used via the adapter member 1000.

Figures 25, 26, 27:
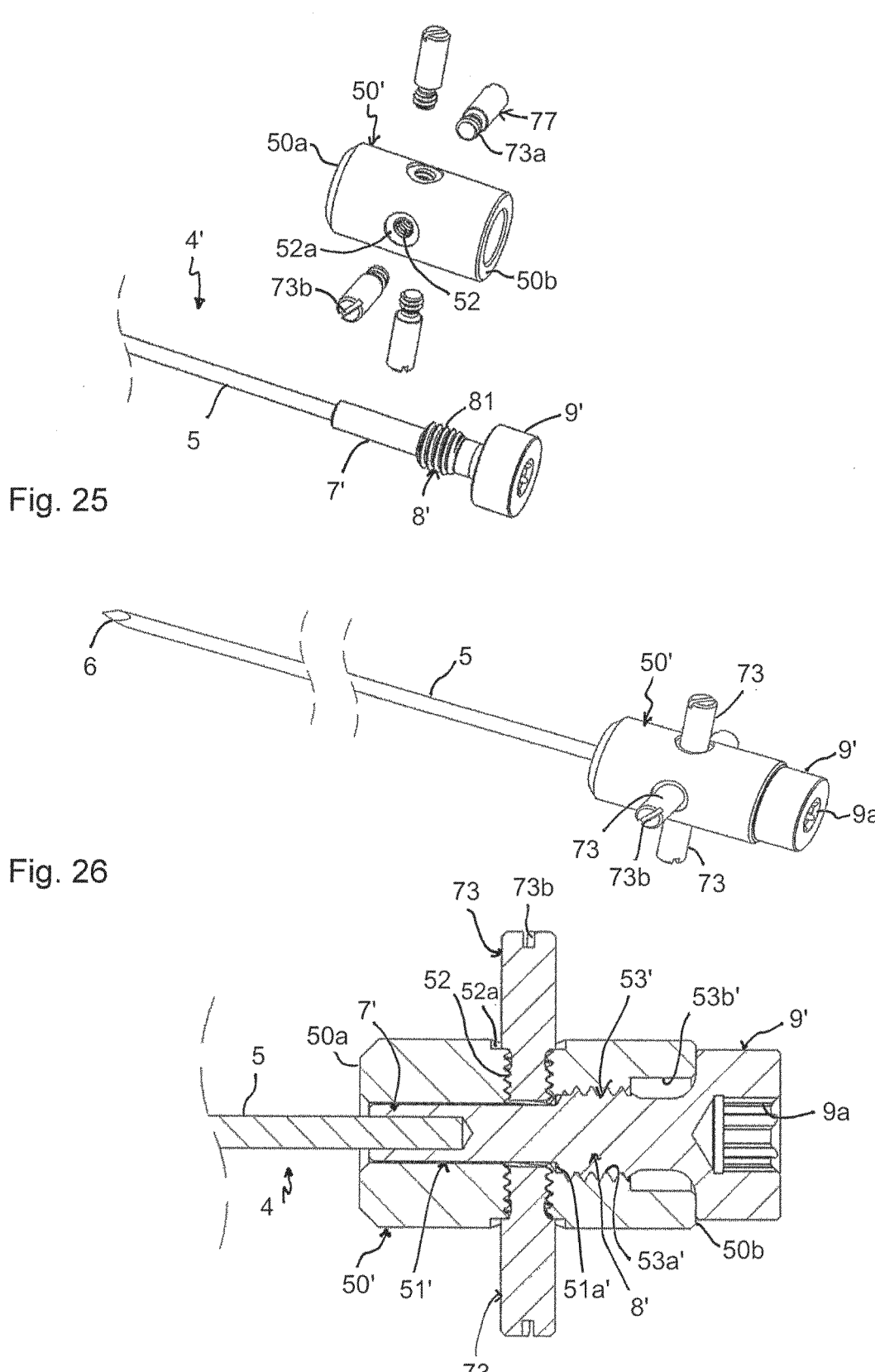
FIG. 25 shows a perspective exploded view of another embodiment of a needle holder and a needle.
FIG. 26 shows a perspective view of the needle holder and the needle of FIG. 25 in an assembled state.
FIG. 27 shows a cross sectional view of the needle holder and the needle of FIGS. 25 and 26, with the needle inserted in the needle holder, the cross-section taken in a plane including a longitudinal axis of the needle.

Referring to FIGS. 25 to 27, a further embodiment of the needle holder and the needle is explained. Parts and portions that are identical or similar to the previous embodiments are indicated with the same reference numerals, and the descriptions thereof will not be repeated. The needle 4' is connectable to the needle holder 50' via a threaded connection. For this purpose, the holding portion of the needle 4' has, between a cylindrical front portion 7' in which the rod portion 5 is supported and a rearward head portion 9', an intermediate threaded portion 8' with an external thread 81. The outer diameter of the threaded portion 8' may be greater than that of the cylindrical front portion 7' and smaller than that of the head portion 9'.

The needle holder 50' is cylindrical, similar to the previous embodiment, and defines a coaxial channel for passing through the rod portion 5 of the needle 4' and for receiving at least part of the holding portion of the needle. A front portion 51' of the channel is configured to receive the cylindrical front portion 7' of the needle. A rear portion 53' of the channel has an internal thread 53a' that is configured to cooperate with the external thread 81 of the holding portion of the needle. The rear portion 53' may be located between the holes 52 for the pins 73 and the rear end 50b. At the transition between the front portion 51' and the rear portion 53' of the channel, a step 51a' may be formed that may serve as an abutment to limit the insertion of the needle into the needle holder 50'. Moreover, when the needle 4' is screwed into the needle holder 50', the needle 4' can be tightened against the abutment. This may result in a stronger and safer connection. Between the rear end 50b and the rear portion 53', a coaxial bore 53b' may be formed, and the head portion 9' may abut against the rear end 50b. The needle holder 50' may be used in the instrument instead of the needle holder 50.

In use, when the needle holder 50' is inserted into the hollow shaft 20, the needle 4' can be removed and/or exchanged by means of screwing the needle into and out of the needle holder. Preferably the needle holder 50' is in the rearmost position when the needle 4' is mounted or exchanged. The threaded connection simplifies the handling of the needle and allows for a quicker exchange of the needle.

Further modifications of the instrument or the parts thereof may be possible. In particular, the shapes of the various parts are not limited to the specific shapes shown in the embodiments. The instrument can also be used, for example, for inserting a syringe for injecting bone cement or other substances after or instead of a needle as shown in the embodiment. For the actuating mechanism, any suitable actuating mechanism that can convert a rotational motion of an actuator into a translational motion of the needle holder can be used. The instrument can also be used in connection with, for example, a drill instead of a shank inserter, or with other suitable surgical instruments. The instrument can also be used without a needle or with needles of different types and lengths.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument for use in surgery, the instrument being connectable to a bone anchor insertion device that comprises a drive shaft configured to engage a bone anchor, the drive shaft defining a coaxial channel for receiving a needle therethrough, the instrument comprising:
    a hollow shaft connectable to the drive shaft along a central axis in a rotationally fixed manner;
    a needle holder configured to hold a needle and movable axially relative to the hollow shaft;
    an actuator movable relative to the hollow shaft; and
    a transmission member connectable to the needle holder and movable axially relative to the actuator for axially advancing and retracting the needle held by the needle holder relative to the hollow shaft, wherein the transmission member comprises a first advancement surface directed at least partially radially inwardly towards the central axis that is engageable with a second advancement surface of the instrument.

2. The instrument of claim 1, wherein the needle holder is positionable at least partially within the hollow shaft and is movable along the central axis relative to the hollow shaft.

3. The instrument of claim 1, wherein the transmission member comprises at least one projection that is configured to extend through a recess in the hollow shaft to engage the needle holder.

4. The instrument of claim 1, wherein the first advancement surface is provided at an inner surface of the transmission member and the second advancement surface is provided at an outer surface of the hollow shaft.

5. The instrument of claim 1, further comprising a handle connectable to the hollow shaft to transmit torque to the hollow shaft.

6. The instrument of claim 5, wherein a portion of the actuator is configured to extend axially into the handle.

7. The instrument of claim 1, wherein the needle holder is configured to releasably receive the needle without disassembling the instrument.

8. The instrument of claim 1, wherein the actuator is rotatable relative to the hollow shaft.

9. The instrument of claim 1, wherein the transmission member is movable relative to the needle holder.

10. The instrument of claim 9, wherein the transmission member is rotatable relative to the needle holder.

11. The instrument of claim 1, wherein the first advancement surface of the transmission member is configured to remain spaced apart from the actuator.

12. An instrument for use in surgery, the instrument being connectable to a bone anchor insertion device that comprises a drive shaft configured to engage a bone anchor, the drive shaft defining a coaxial channel for receiving a needle therethrough, the instrument comprising:
    a hollow shaft connectable to the drive shaft in a rotationally fixed manner;
    a needle holder configured to hold a needle and movable axially relative to the hollow shaft;
    an actuator movable relative to the hollow shaft; and
    a transmission member connectable to the needle holder and movable axially relative to the actuator, wherein the transmission member comprises a first advancement surface engageable with a second advancement surface of the hollow shaft for axially advancing and retracting the needle held by the needle holder relative to the hollow shaft, and a position indicator visible from outside the instrument through a window formed in a part of the instrument different from the transmission member to indicate a relative position of the needle holder relative to the hollow shaft.

13. The instrument of claim 12, wherein the actuator is rotatable relative to the hollow shaft.

14. The instrument of claim 12, further comprising a handle connectable to the hollow shaft to transmit torque to the hollow shaft.

15. The instrument of claim 14, wherein the window is formed in the handle.

16. The instrument of claim 12, wherein at least part of the transmission member is positionable in at least part of the actuator.

17. The instrument of claim 16, wherein the position indicator is ring-shaped and is positionable around part of the actuator.

18. An instrument for use in surgery, the instrument being connectable to a bone anchor insertion device that comprises a drive shaft configured to engage a bone anchor, the drive shaft defining a coaxial channel for receiving a needle therethrough, the instrument comprising:

a hollow shaft defining a recess configured to receive and end of the drive shaft to connect the hollow shaft to the drive shaft in a rotationally fixed manner;

a needle holder configured to hold a needle and movable axially relative to the hollow shaft;

an actuator movable relative to the hollow shaft; and a transmission member connectable to the needle holder and movable axially relative to the actuator, wherein the transmission member comprises a first advancement surface engageable with a second advancement surface of the instrument for axially advancing and retracting the needle held by the needle holder relative to the hollow shaft;

wherein the recess of the hollow shaft extends axially into the actuator, such that at least part of the recess is configured to be located at a same axial position as at least part of the actuator to reduce an overall axial length of the instrument.

19. The instrument of claim 18, wherein the actuator is rotatable relative to the hollow shaft.

20. The instrument of claim 18, further comprising a separate connector configured to facilitate insertion and fixation of the drive shaft into the recess of the hollow shaft, wherein at least part of the connector is configured to extend axially into the actuator.

* * * * *